(12) United States Patent
Green et al.

(10) Patent No.: US 6,858,018 B1
(45) Date of Patent: Feb. 22, 2005

(54) IONTOPHORETIC DEVICES

(75) Inventors: Philip G. Green, Cliffside, NJ (US);
Ronald J. Pettis, Durham, NC (US);
Michelle R. Brosnan-Cook, Cary, NC (US)

(73) Assignee: Vyteris, Inc., Fair Lawn, NJ (US)

( * ) Notice: Subject to any disclaimer, the term of this patent is extended or adjusted under 35 U.S.C. 154(b) by 0 days.

(21) Appl. No.: 09/162,301

(22) Filed: Sep. 28, 1998

(51) Int. Cl.$^7$ ............................................. A61N 1/30
(52) U.S. Cl. ........................................ 604/19; 604/20
(58) Field of Search ............................... 424/449, 448; 604/19, 20

(56) References Cited

U.S. PATENT DOCUMENTS

| | | | |
|---|---|---|---|
| 4,141,359 A | 2/1979 | Jacobsen et al. | 128/172.1 |
| 4,588,580 A | 5/1986 | Gale et al. | 424/21 |
| 4,593,053 A | 6/1986 | Jevne et al. | 523/111 |
| 5,006,108 A | 4/1991 | LaPrade | 604/20 |

(List continued on next page.)

FOREIGN PATENT DOCUMENTS

| | | |
|---|---|---|
| EP | 0 904 779 A2 | 3/1999 |
| GB | 2 239 803 A | 7/1991 |
| WO | WO 96/39224 | 12/1996 |
| WO | WO 97/33645 | 9/1997 |
| WO | WO 98/26760 | 6/1998 |

OTHER PUBLICATIONS

Southam et al., Device for Transdermal Administration of Supentanil by Electrotransport, Neth. Appl., 1997.*

(List continued on next page.)

*Primary Examiner*—Thurman K. Page
*Assistant Examiner*—Konata M. George (74) *Attorney, Agent, or Firm*—Kirkpatrick & Lockhart LLP

(57) ABSTRACT

Iontophoretic devices for the delivery of N-phenyl-N-(4-piperidinyl)amide esters are provided. The N-phenyl-N-(4-piperidinyl)amide esters are compounds of the 1. A reservoir comprising a matrix material and, distributed in said matrix material, a pharmaceutically acceptable amount of at least one compound selected from compounds of the formula (I)

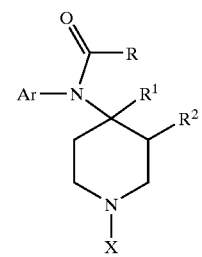

wherein:
X is a member selected from the group consisting of alkoxy-carbonyl-lower alkyl, lower alkyl-carbonyloxy-lower alkyl, alkenyloxy-carbonyl-lower alkyl, and $(C_{1-2})$alkoxy-$(C_{1-2})$alkoxy-carbonyl-lower alkyl;
Ar is a member selected from the group consisting of phenyl, and mono-, di- and tri-substituted phenyl, wherein each substituent is independently selected from the group consisting of halo, lower alkyl, lower alkoxy and trifluoromethyl;
R is a member selected from the group consisting of lower alkyl, and lower alkoxy-lower alkyl,;
$R^1$ is a member selected from the group consisting of hydrogen, lower alkoxy-carbonyl; and
$R^2$ is a member selected from the group consisting of hydrogen and methyl; and the optically active and cis-trans isomers thereof, and the acid addition salts, of said compounds and isomers.

11 Claims, 2 Drawing Sheets

U.S. PATENT DOCUMENTS

| | | | |
|---|---|---|---|
| 5,019,583 A | 5/1991 | Feldman et al. | 514/327 |
| 5,047,007 A | 9/1991 | McNichols et al. | 604/20 |
| 5,080,546 A | 1/1992 | Purvin et al. | 411/156 |
| 5,135,479 A | 8/1992 | Sibalis et al. | 604/20 |
| 5,143,071 A | 9/1992 | Keusch et al. | 128/640 |
| 5,169,382 A | 12/1992 | Theeuwes et al. | 604/20 |
| 5,203,768 A * | 4/1993 | Haak et al. | 604/20 |
| 5,224,927 A | 7/1993 | Tapper | 604/20 |
| 5,224,928 A | 7/1993 | Sibalis et al. | 604/20 |
| 5,232,438 A | 8/1993 | Theeuwes et al. | 604/20 |
| 5,246,418 A | 9/1993 | Haynes et al. | 604/20 |
| 5,254,081 A | 10/1993 | Maurer et al. | 604/20 |
| 5,320,597 A | 6/1994 | Sage, Jr. et al. | 604/20 |
| 5,358,483 A | 10/1994 | Sibalis | 604/20 |
| 5,688,232 A | 11/1997 | Flower | 604/20 |
| 5,693,024 A | 12/1997 | Flower | 604/20 |
| 5,738,647 A | 4/1998 | Bernhard et al. | 604/20 |
| 5,882,677 A * | 3/1999 | Kupperblatt | 424/449 |
| 5,910,301 A * | 6/1999 | Farr et al. | 424/45 |

OTHER PUBLICATIONS

Suneel K. Gupta et al., Effect of Current Density on Pharmacokinetics Following Continuous or Intermittent Output from a Fentanyl Electrotransport System, *Journal of Pharmaceutical Sciences*, vol. 87, No. 8, Aug. 1998, pp. 976–981 (published on Web Jun. 13, 1998), American Chemical Society and American Pharmaceutical Association.

Hartmut Bürkle et al., Remifentanil: A Novel, Short–Acting μ–Opioid, *Anesthesia and Analgesia*, 83: pp. 646–651, (1996), International Anesthesia Research Society.

Sanjay S. Patel et al., Remfentanil, *Drugs*, Sep. 1996; 52 (3): pp. 417–427, (1996) Adis International Limited.

Hartmut Buerkle et al, Continuous Intrathecal Administration of Shortlasting μ Opiods Remifentanil and Alfentanil in the Rat, *Anesthesiology*, 84: pp. 926–935, (1996), American Society of Anesthesiologists, Inc., Lippencott–Raven Publishers.

Sophie Thysman et al., Transdermal iontophoresis of fentanlyl: delivery and mechanistic analysis, *International Journal of Pharmaceutics*, 101: pp. 105–113 (1994), Elsevierier Science Publishers B.V.

Sophie Thysman et al., In Vivo Iontophoresis of Fentanyl and Sufentanil in Rats: Pharmacokinetics and Acute Antinociceptive Effects, *Anesthesia and Analgesia*, 77: pp. 61–66 (1993), International Anesthesia Research Society.

Véronique Préat et al., Transdermal iontophoretic delivery of sufentanil, *International Journal of Pharmaceutics*, 96: pp. 189–196 (1993), Elsevier Science Publishers B.V.

Geoffrey K. Gourlay et al., The transdermal administration of fentanyl in the treatment of postoperative pain: pharmacokinetics and pharmacodynamic effects, *Pain*, 37: pp. 193–202 (1989), Elsevier.

P.S. Sebel et al., Transdermal Absorption of Fentanyl and Sufentanil in Man, *European Journal of Clinical Pharmacology*, 32: pp. 529–531 (1987), Springer–Verlag.

Paul A. Janssen, The Development Of New Synthetic Narcotics, *Opioids in Anesthesia*, pp. 37–44 (Estafanous, F.G., ed.) Butterworth Publishers (1984).

L.E. Mather, Clinical Pharmacokinetics of Fentanyl and its Newer Derivatives, *Clinical Pharmacokinetics*, 8: pp. 422–446 (1983), ADIS Press Austalasia Pty Ltd.

* cited by examiner

IONTOPHORETIC DEVICES

FIELD OF THE INVENTION

This invention relates generally to iontophoretic devices. Specifically, this invention relates to intophoretic devices for delivery of a certain class of drugs. More specifically, this invention relates to iontophoretic devices for delivery of N-phenyl-N-(4-piperidinyl)amide esters.

BACKGROUND OF THE INVENTION

The transdermal delivery of drugs, by diffusion through the epidermis, offers improvements over more traditional delivery methods, such as subcutaneous injections and oral delivery. Transdermal drug delivery avoids the hepatic first pass effect encountered with oral drug delivery. Transdermal drug delivery also eliminates patient discomfort associated with subcutaneous injections. In addition transdermal delivery can provide more uniform concentrations of drug in the bloodstream of the patient over time due to the extended controlled delivery profiles of certain types of transdermal delivery devices. The term "transdermal" delivery, broadly encompasses the delivery of an agent through a body surface, such as the skin, mucosa, or nails of an animal.

The skin functions as the primary barrier to the transdermal penetration of materials into the body and represents the body's major resistance to the transdermal delivery of therapeutic agents such as drugs. To date, efforts have been focussed on reducing the physical resistance or enhancing the permeability of the skin for the delivery of drugs by passive diffusion. Various methods for increasing the rate of transdermal drug flux have been attempted, most notably using chemical flux enhancers.

Other approaches to increase the rates of transdermal drug delivery include use of alternative energy sources such as electrical energy and ultrasonic energy. Electrically assisted transdermal delivery is also referred to as electrotransport. The term "electrotransport" as used herein refers generally to the delivery of an agent (e.g., a drug) through a membrane, such as skin, mucous membrane, or nails wherein the delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid, which liquid contains the agent to be delivered, under the influence of an electric field. Still another type of electrotransport process electroporation, involves the formation of transiently-existing pores in a biological membrane by the application of an electric field. An agent can be delivered through the pores either passively (i.e., without electrical assistance) or actively (i.e., under the influence of an electric potential). However, in any given electrotransport process, more than one of these processes, including at least some "passive" diffusion, may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, whatever the specific mechanism or mechanisms by which the agent actually is transported.

Electrotransport devices use at least two electrodes that are in electrical contact with some portion of the skin, nails, mucous membrane, or other surface of the body. One electrode, commonly called the "donor" electrode, is the electrode from which the agent is delivered into the body. The other electrode, typically termed the "counter" electrode or "indifferent" electrode, serves to close the electrical circuit through the body. For example, if the agent to be delivered is positively charged, i.e. a cation, then the anode is the donor electrode, while the cathode is the counter electrode which serves to complete the circuit. Alternatively, if an agent is negatively charged, i.e., an anion, the cathode is the donor electrode and the anode is the counter electrode. Additionally, both the anode and cathode may be considered donor electrodes if both anionic and cationic agent ions, or if uncharged dissolved agents, are to be delivered.

Furthermore, electrotransport delivery systems generally require at least one reservoir or source of the agent to be delivered to the body. Examples of such donor reservoirs include a pouch or cavity, a porous sponge or pad, or a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically at any one time, one pole of the power source is electrically connected to the donor electrode, while the opposite pole is electrically connected to the counter electrode. Since it has been shown that the rate or electrotransport drug in delivery is approximately proportional to the electric current applied by the device, many electrotransport devices typically have an electrical controller that controls the voltage and/or current applied through the electrodes, thereby regulating the rate of drug delivery. These control circuits use a variety of electrical components to control the amplitude, polarity, timing, waveform shape, etc. of the electric current and/or voltage supplied by the power source. See, for example, Flower, U.S. Pat. No. 5,688,232, and McNichols, et al., U.S. Pat. No. 5,047,007.

To date, commercial transdermal electrotransport drug delivery devices (e.g., the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a biocompatible electrolyte salt. The power supply unit has electrical controls for adjusting the amount of electrical current applied through the electrodes. The "satellite" electrodes are connected to the electrical power supply unit by long (e.g., 1–2 meters) electrically conductive wires or cables. The wire connections are subject to disconnection and limit the patient's movement and mobility. Wires between electrodes and controls may also be annoying or uncomfortable to the patient. Other examples of desktop electrical power supply units which use "satellite" electrode assemblies are disclosed in Jacobsen et al., U.S. Pat. No. 4,141,359 (see FIGS. 3 and 4): LaPrade, U.S. Pat. No. 5,006,108 (see FIG. 9): and Maurer et al., U.S. Pat. No. 5,254,081.

More recently, small self-contained electrotransport delivery devices have been proposed to be worn on the skin, sometimes unobtrusively under clothing, for extended periods of time. Such small self-contained electrotransport delivery devices are disclosed for example in Tapper, U.S. Pat. No. 5,224,927; Sibalis, et al., U.S. Pat. No. 5,224,928; and Haynes et al., U.S. Pat. No. 5,246,418.

There have recently been suggestions to utilize electrotransport devices having a reusable controller which is adapted for use with multiple drug-containing units. The drug-containing units are simply disconnected from the controller when the drug becomes depleted and a fresh drug-containing unit is thereafter connected to the controller. In this way, the relatively more expensive hardware components of the device (e.g., batteries, LED'S, circuit hardware, etc.) can be contained within the reusable controller, and the relatively less expensive donor reservoir and counter reservoir matrices can be contained in the single use/disposable drug-containing unit, thereby bringing down the overall cost of electrotransport drug delivery. Examples of electrotransport devices comprised of a reusable controller, removably connected to a drug-containing unit are disclosed in Sage, Jr., et al., U.S. Pat. No. 5,320,597; Sibalis, U.S. Pat. No. 5,358,483; Sibalis, et al., U.S. Pat. No. 5,135,479 (FIG. 12); and Devane, et al., UK Patent Application 2 239 803.

In further development of electrotransport devices, hydrogels have become particularly favored for use as the drug and electrolyte reservoir matrices, in part, due to the fact that water is the preferred liquid solvent for use in electrotransport drug delivery due to its excellent biocompatiblity compared with other liquid solvents such as alcohols and glycols. Hydrogels have a high equilibrium water content and can quickly absorb water. In addition, hydrogels tend to have good biocompatibility with the skin and with mucosal membranes.

Of particular interest in transdermal delivery is the delivery of drugs for the management of moderate to severe pain. Control of the rate and duration of drug delivery is particularly important for transdermal delivery of pain control medications to avoid the potential risk of overdose and the discomfort of an insufficient dosage.

One class of pain control medications that has found application in a transdermal delivery route is the synthetic opiates, a group of 4-aniline piperidines, specifically fentanyl and sufentanil. These synthetic opiates are characterized by their relatively rapid onset of analgesia, relatively high potency, and relatively short duration of action compared to morphine. The delivery of fentanyl and sufentanil by various transdermal routes has been reported in the literature. See for example, PCT application 96/39224; Thysman and Preat (Anesth. Analg. 77(1993)pp.8146); Thysman et al. Int. J. Pharma., 101(1994) pp. 105–113; V. Preat et al. Int. J Pharm., 96(1993) pp. 189–196 (sufentanil); Gourlav et al. Pain, 37 (1989) pp. 193–202 (fentanyl); Sebel et al. Eur J. Clin. Pharmacol. 32(1967) pp.529–531 (fentanyl and sufentanil); Gale, et al., U.S. Pat. No. 4,588,580, and Theeuwes et al, U.S. Pat. No. 5,232,438.

While fentanyl and sufentanil are useful analgesics, there are certain drawbacks associated with their use. For instance, it is desirable to deliver analgesics which are as potent as fentanyl and sufentanil but have a shorter plasma half-life (i.e. duration of effect). Analgesics which demonstrate shorter plasma half-lives have increased safety margins for dosing because of the speed with which they are cleared from the system. They also shorten the offset and recovery period after dosing because the rapid clearing of the drug results in a lack of accumulation in the system. This has the further advantage of minimizing the potential for abuse, reducing the risk of increased tolerance to the drug, and reducing the extent of any negative opiod side effects.

It is an object of the present invention to provide an iontophoretic device which overcomes the drawbacks associated with the iontophoretic delivery of fentanyl and sufentanil.

BRIEF SUMMARY OF THE INVENTION

The present invention provides a reservoir comprising a matrix material and, distributed in said matrix material, a pharmaceutically acceptable amount of at least one compound selected from compounds of the formula (I)

wherein:

X is a member selected from the group consisting of: alkoxy-carbonyl-lower alkyl (preferred), lower alkyl-carbonyloxy-lower alkyl, alkenyloxy-carbonyl-lower alkyl, and $(C_{1-2})$alkoxy-$(C_{1-2})$alkoxy-carbonyl-lower alkyl;

Ar is a member selected from the group consisting of phenyl, and mono-, di- and tri-substituted phenyl, preferably mono-substituted in the 2-position, wherein each substituent is independently selected from the group consisting of halo, lower alkyl, lower alkoxy and trifluoromethyl;

R is a member selected from the group consisting of lower alkyl, preferably ethyl, and lower alkoxy-lower alkyl, preferably methoxymethyl;

$R^1$ is a member selected from the group consisting of hydrogen, lower alkoxy-carbonyl, preferably methoxycarbonyl, and methoxymethyl; and $R^2$ is a member selected from the group consisting of hydrogen and methyl; and the optically active and cis-trans isomers thereof, and the acid addition salts, of said compounds and isomers.

The present invention further comprises an iontophoretic device comprising:

(a) a donor reservoir comprising a matrix material and, distributed in said matrix material, a pharmaceutically acceptable amount of at least one compound selected from compounds of the formula (I) as set forth above;

(b) a current distributing member in electrical communication with the donor reservoir;

(c) an indifferent electrode; and (d) an electrical power source in electrical connection with the current distributing member and the indifferent electrode.

DETAILED DESCRIPTION OF THE INVENTION

We have surprisingly found that the compounds recited above, despite their relatively poor chemical stability and enzymatic stability, can be successfully delivered by iontophoresis to impart analgesic and/or anestheic effects. These compounds are known, for example, from U.S. Pat. No. 5,019,583, the disclosure of which is hereby incorporated by reference herein.

As used in the foregoing definitions the term "lower" is meant to modify the so-indicated group by indicating from 1 to 4 carbon atoms; the terms "alkyl", "alkoxy" and "alkenyl" are each meant to respectively include straight and branch chained hydrocarbons, e.g. of about 1 to 10 carbons and include the group of hydrocarbons of 1 to 4 carbons; and the term "halo" is generic to halogens of atomic weight less than 127, i.e., fluoro, chloro, bromo and iodo.

The compounds of formula (I) provide potent analgesia and/or anesthesia with a duration of action ranging from ultra-short to medium. Such activity is characterized by rapid onset and a half-life generally ranging from about 5 to about 40 minutes in experimental rats. In contrast, the well-known narcotic analgesic, N-(1-phenethyl-4-piperidyl) propionanilide, generically known as fentanyl, and its congeners, sufentanil and alfentanil, have durations of action of 60, 80 and 55 minutes in rats, respectively, and terminal half-lives in humans of about 1.5 to 7 (16 for geriatric patients), 2.5 and 1.2 to 3 hours, respectively (Mather, L. E., Clinical Pharmacokinetics, 1983, 8:422446). The marked potency and very short duration of effects provided by the ultra-short acting compounds useful in this invention are highly desirable in circumstances where severe pain has to be eliminated over a short period of time, e.g., anesthesiology. With the current preponderance of short surgical procedures and the growing trend towards outpatient surgery, there exists an urgent need for the delivery of a powerful but short acting pain control medications as stated by Dr. Paul A. J. Janssen in Janssen: Opioids in Anesthesia. (Estafanous, F. G., ed.) Butterworth, Boston. (1984). The compounds useful in the present invention can be delivered iontophoretically to mammals such as man in amounts sufficient to provide analgesic and/or anestheic effects.

When X is alkoxy-carbonyl-lower alkyl, e.g. lower alkoxy-carbonyl-lower alkyl, compounds wherein the carbon of the alkoxy directly attached to the oxygen of the alkoxy is a methylene or methyl group, i.e. wherein it is substituted by no more than 1 alkyl group, are generally shorter acting. Preferably, the lower alkyl of the alkoxy-carbonyl-lower alkyl is ethyl of the formula —$CH_2CH_2$—.

The compounds of formula (I) may be converted to the therapeutically active acid addition salt form by treatment with an appropriate acid, such as, for example, an inorganic acid, such as hydrohalic acid, e.g., hydrochloric, hydrobromic, and the like, and sulfuric acid, nitric acid, phosphoric acid and the like; or an organic acid, such as, for example, acetic, propanoic, hydroxyacetic, alpha-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, alpha-hydroxy-benzeneacetic, methanesulfonic, ethanesulfonic, benzenesulfonic, 4-methylbenzenesulfonic, cyclohexanesulfamic, alpha-hydroxybenzoic, 4-amino-2-hydroxybenzoic and the like acids. Conversely, the salt form can be converted by treatment with alkali into the free base form. In addition, the salt forms may be useful in the preparation of other salt forms, for example, as intermediates for conversion into the preferred pharmaceutically acceptable salt derivatives. Furthermore, the particular salt may exist as a solvate, e.g., a hydrate or a hemihydrate. Preferably, the compounds for use in the present invention are in the form of a pharmaceutically acceptable salt, most preferably the hydrochloride salt. Salts are preferred, in part, because they have a higher charge and are more mobile when an electric charge is applied.

All racemic and isomeric forms of the compounds of formula (I), including diastereomeric mixtures, pure diastereomers and enantiomers, and mixtures thereof, are useful for the present invention. In general, it is preferred that the compounds for use in the present invention are in the form of a pharmacologically acceptable salt. The preferred compounds of formula (I) for use in the present invention are those wherein X is $CH_2CH_2COOCH_3$. Most preferably, the compound of formula (I) for use in the present invention is the hydrochloride salt of the compound wherein X is $CH_2CH_2COOCH_3$, R is $OCH_3$, $R^1$ and $R^2$ are both H, and Ar is phenyl. This compound is referred to as remifentanil hydrochloride, or RemiHCl, throughout the remainder of the specification and claims.

The compounds useful in the present invention are distributed in a matrix material. Suitable matrix materials for the present invention include liquid, semi-liquid, semi-solid, or solid materials. Preferably the matrix material is a semi-solid material such as a gel or other polymeric material, for example, polyvinylpyrrolidones, polvinyl alcohol, polyethylene oxides such as Polyox® manufactured by Union Carbide Corp., Carbopols® manufactured by BF Goodrich of Akron, Ohio, blends of polyethylene oxide or polyethylene glycols with polyacrylic acid such as Polyox blended with Carbopols, polyacrylamide, Klucel, cross-linked dextran such as Sephadex (Pharmacia Fine Chemicals, AB, Uppsala, Sweden); Water Lock® (Grain Processing Corp., Muscatine, Iowa) which is a starch-graft-poly(sodium acrylate-co-acrylamide)polymer; cellulose derivatives such as hydroxyethyl cellulose, hydroxypropylmethylcellulose, low substituted hydroxypropylcellulose, and crosslinked Na-carboxymethylcellulose; hydrogels such as polyhydroxyethyl methacrylate, natural gums, chitosan, pectin, starch, guar gum, locust bean gum, and the like, and combinatons and blends thereof. Preferred hydrogels are crosslinked hydrogels described, for example, in U.S. Pat. No. 5,143,071 to Keusch, et al. and commonly assigned copending patent application Ser. No. 08/533,979 filed Sep. 26, 1995, the disclosures of which are hereby incorporated by reference herein. The most preferred hydrogels are crosslinked polyvinylpyrrolidone and polyvinyl alcohols. Solid, materials, particularly porous polymers may also be use for the matrix material. Suitable porous polymers can be made, for example, from polyethylene, polypropylene, polyvinylidene fluoride, polytetrafluoroethylene, nylons or polyethersulfones.

The compound may be distributed in the matrix material by any suitable means. A preferred means for distributing the compound in the matrix material is by adding a solution or dispersion of the compound to the matrix material. When the matrix material is relatively porous, the solution or dispersion of the compound is readily absorbed throughout the pores of the matrix. The compound is generally added to the matrix material in an amount of from 0.01 milligrams to 1000 milligrams, preferably in an amount of from 0.1 to 100 milligrams.

When used in an iontophoretic device, the reservoir of the present invention must be sufficiently hydrated to permit the flow of ions therethrough. In most cases, the liquid used to hydrate the reservoir is water, but other liquids can also be used to "hydrate" (i.e. activate) the reservoir. The liquid may be present from a solution or dispersion of the compound, from the matrix material, added separately before or after distributing the compound in the matrix material or a combination thereof. Other methods for hydrating an iontophoretic reservoir are shown, for example, in U.S. Pat. Nos. 5,738,647 and 5,693,024, the disclosures of which are hereby incorporated by reference herein.

The construction of the donor reservoir must be consistent with the requirements for ionic communication with the epithelial surface and electrical communication with the current distribution member. Accordingly, the structure of the donor reservoir would vary, depending upon the desired application. As discussed above, the matrix material of the donor reservoir may include a liquid, semi-liquid, semi-solid, or solid material. With a flowable material, the donor reservoir preferably further comprises means for at least substantially inhibiting the flow of the contents out of the reservoir. In such situations, the flow of the contents is desirably minimized when the device is in storage. For example, a membrane may be deployed to surround the contents of the donor reservoir. In certain situations the flow of the contents of the reservoir may be minimized while in storage, but increased in use. For example, a surrounding membrane may increase in porosity, permeability, or conductivity upon the application of an electric field across the membrane. Examples of such membranes are disclosed in U.S. Pat. Nos. 5,080,546; 5,169,382; and 5,232,438, the disclosures of which are incorporated by reference herein.

The donor reservoir can have a monolithic structure or it can be separated into two or more areas. Preferably, the donor reservoir is separated into two or more areas, with the matrix containing the drug situated so that it can be placed in direct contact with the epithelial surface. When separated into two or more areas, it may be desirable to use a semi-permeable membrane to separate the two or more areas. For instance, one preferred structure for the donor reservoir has an electrolyte reservoir atop the drug-containing matrix separated by a semi-permeable membrane. In such a construction, it is desirable to have the current distributing member in current distributing communication with the electrolyte reservoir. Any of the materials suitable for the matrix can be used for the electrolyte reservoir. In addition, the electrolyte reservoir, and optionally the drug-containing matrix material, should contain one or more electrolytes, polyelectrolytes or a combinaton thereof, which are ionic or ionizable components which can act to conduct current towards or away from the current distributing member. Typically, the electrolyte or polyelectrolyte may comprise one or more mobile ions, the selection of which depends on the desired application. Alternatively, they may comprise materials which are relatively immobile in the absence of an electric field, but which act to deliver mobile ions in the presence of an electric field. Such relatively immobile electrolytes and polyelectrolytes are commonly referred to as an "ion source."

Suitable electrolytes and polyelectrolytes include, for example, aqueous solutions of salts. A preferred electrolyte is an aqueous solution of sodium chloride having a concentration of less than 1 mole per liter, more preferably at about physiological concentration. Other electrolytes include salts of physiological ions, including, but not limited to, potassium, chloride, and phosphate. Ion sources include, for example, certain polyelectrolytes, ion exchange membranes and resins, non-ionic buffers which become ionic upon pH change, and other conventional ion sources.

In addition to the compound and the matrix material, it may be desirable to include one or more additional components in the reservoir. Such additional components may include, for example, a buffer. The ion of the buffer of like charge to the drug ion should have low ionic mobility. The limiting ionic mobility of this ion is preferably no greater that $1 \times 10^{-4}$ cm$^2$/volt-sec. The donor reservoir may also contain an amount of an ion which can compete with the compound; if present, the amount of the ion should be sufficient for controlling the flux profile of the compound being delivered. Other optional components of the reservoir include, for example, chelating agents such as EDTA or citrate ions, surfactants, ionic excipients, osmolarity adjusters such as polyethylene glycols and sugars, ionic antibiotics, penetration enhancers, stabilizers, solubility enhancers such as cyclodextrins or chitosan, anti-oxidants, enzyme inhibitors, preservatives, and thickening agents. In the case of RemiHCl, it is preferred that the donor reservoir is buffered to maintain the pH of the donor reservoir below 8.0, more preferably below 7.07, most preferably, in the range of from 2 to 6.5.

An ionic drug can be delivered from either the anode, the cathode, or both simultaneously. For example, if the compound to be driven into the body is positively charged, then the positive electrode or anode will be the active electrode and the negative electrode or cathode will serve to complete the electrochemical circuit. Alternatively, if the compound to be delivered is negatively charged, then the negative electrode will be the active electrode and the positive electrode will be the indifferent electrode. Alternatively, the drug formulation may contain an amount of an ion which will compete with the compound, the amount of the ion should be sufficient for controlling the flux profile of the compound being delivered.

In preferred embodiments, the donor reservoir is constructed to retain its physical integrity and to inherently resist migration and loss of the compound. Such embodiments include those in which the donor reservoir includes a solid or semi-solid material such as a gel or other polymeric material. In an especially preferred embodiment, the ionized substance reservoir includes a polymeric film in which the substance to be iontophoretically delivered is dispersed. The mobility of the substance to be delivered is substantially increased by the application of the electric field, permitting effective delivery across the target epithelial surface. Such a film need not contain any significant additional amount of hydrating material. In preferred embodiments, a cross-linked hydrogen is used as the matrix material, and if present, in the electrolyte reservoir, because it inherently contains significant amounts of water, which can serve as a water reservoir during iontophoresis.

Alternatively, the electrolyte reservoir may contain counterions that form a soluble salt with an electrochemically generated ion. For example, in an apparatus employing a silver anodal current distributing member, a suitable counterion might be acetate or nitrate. Such counterions are useful when other means are provided for sequestering electrochemically generated ions.

Thus, the electrolyte reservoir can provide at least one ion of the same charge as the electrochemically generated ion, to permit current to be conducted, and at least one oppositely charged ion.

A compound of formula (I) can be delivered from either the anode, the cathode, or both simultaneously. For example, if the compound to be driven into the body is positively charged, then the positive electrode or anode will be the donor, or "active", electrode and the negative electrode or cathode will serve to complete the electrochemical circuit. Alternatively, if the compound to be delivered is negatively charged, then the negative electrode will be the active electrode and the positive electrode will be the indifferent electrode.

The reservoir containing the compound is placed in drug transmitting relation to the body surface of the patient. While the reservoir is in drug transmitting relation to the body surface of the patient and the conductive member is applied to the reservoir, a positive voltage is applied to the conductive member to drive the ionic drug through the body surface of the patient.

The Current Distributing Member (Active Electrode)

The iontophoretic device of the invention includes a current distributing member which conveys electrical current into the reservoir for the delivery of the compound. The current distributing member may suitably be constructed of any of a large variety of electrically conductive materials, including both inert and sacrificial materials.

Inert conductive materials are those electrically conductive materials which, when employed in the iontophoretic devices of the invention, do not themselves undergo or participate in electrochemical reactions. Thus, an inert material distributes current without being eroded or depleted due to the distribution of current, and conducts current through generating ions by either reduction or oxidation of water. Inert conductive materials typically include, for example, stainless steel, platinum, gold, and carbon or graphite.

Alternatively, the current distributing member may be constructed from a sacrificial conductive material. A material may be considered sacrificial if, when employed as an electrode in an iontophoretic device of the invention, the material is eroded or depleted due to its oxidation or reduction. Such erosion or depletion occurs to when the materials and formulations used in the iontophoresis device enable a specific electrochemical reaction, such as when a silver electrode is used with a formulation containing chloride ions. In this situation, the current distributing member would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes may also be employed. In such cases, the metal would oxidize to metal ions, which would then be precipitated as an insoluble salt.

For cathodes, the current distributing member may be constructed from any electrically conductive material provided an appropriate electrolyte formulation is provided. For example, the cathodic current distributing member may be constructed from a metal/metal salt material. A preferred cathodic material is a silver/silver halide material. In such embodiments, a metal halide salt is preferably employed as the electrolyte. In this case, the device would electrochemically generate halide ions from the electrode as the metal halide salt is reduced. Also, accompanying silver ions in a formulation would be reduced to silver metal and would deposit (plate) onto the electrode. In other embodiments, the cathode material may be an intercalation material, an amalgam, or other material which can take electrolyte cations such as sodium out of solution, below the reduction potential of water. In addition, other materials may be used which permit the plating out of a metal from the appropriate electrolyte solution. Thus, metals such as silver, copper, zinc, and nickel, and other materials, such as carbon, may be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context.

Additional types of materials useful as current distributing members according to the invention are disclosed in detail in a co-pending application entitled Low-Cost Electrodes for an Iontophoretic Device, by V. Reddy et al., Ser. No. 08/536,029, filed on Sep. 29, 1995, the disclosure of which is incorporated by reference herein.

The current distributing member may take any form known in the art, such as the form of a plate, foil layer, screen, wire, or dispersion of conductive particles embedded in a conductive matrix.

Indifferent Electrode

Iontophoretic devices require at least two electrodes to provide a potential to drive compounds into the skin of a patient. Both electrodes are disposed to be in intimate electrical contact with the skin thereby completing the electrochemical circuit formed by the anode and cathode of the iontophoretic device. The electrodes may be further defined as an active electrode, discussed above, from which a compound is delivered into the body, and an indifferent or ground electrode that serves to complete the electrochemical circuit. Any of the materials described above for the active electrode may be used for the indifferent electrode. Furthermore, it is often desirable to have the indifferent electrode be in electrical contact with a reservoir containing one or more electrolytes capable of conducting ions from the epithelial surface to the indifferent electrode. Any of the materials suitable for the donor reservoir may also be used for an electrolyte reservoir for the indifferent electrode.

The active electrode and the indifferent electrode are connected to an electrical power source. The electrical power source may be, for example, one or more batteries, or direct electrical supply. In addition, the electrical power source may be connected to a controller capable of controlling the current supplied from the electrical power source.

Protective Backing

The iontophoretic apparatus of the invention may also include a suitable backing film positioned on top of the electrolyte reservoir. The backing film provides protection against contamination and damage to the current distributing member, if present, and the electrolyte reservoir of the apparatus.

Release Liner

The iontophoretic apparatus of the invention optionally includes a release liner which may be fixed to the underside of the donor reservoir by an adhesive. The release liner protects the surface of the donor reservoir which contact the epithelial surface from contamination and damage when the device is not in use. When the device is ready for use, the release liner may be peeled off to expose the epithelial contacting surface of the donor reservoir for application of the device to a patient.

Figure 1:
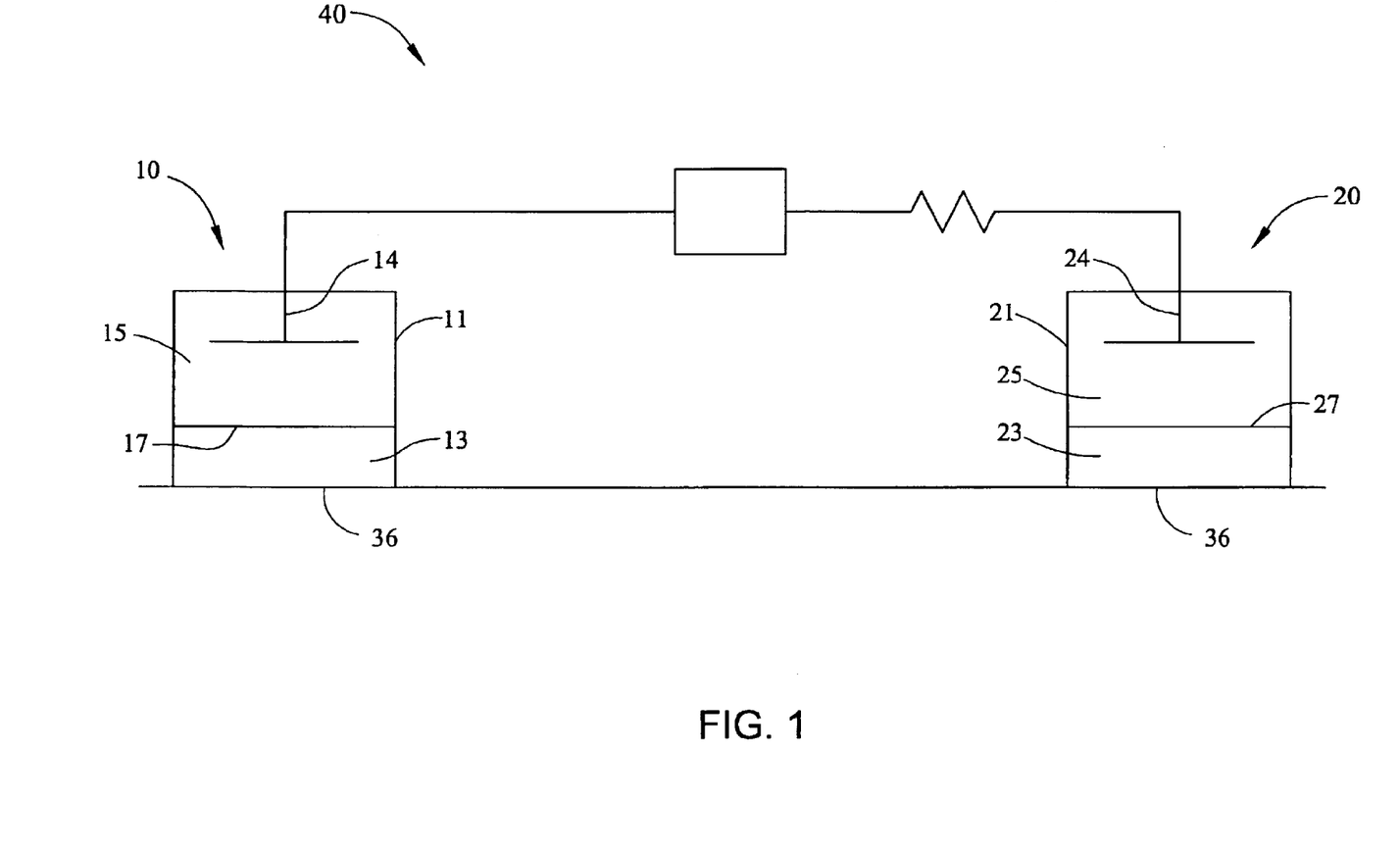
FIG. 1 depicts an iontophoretic device according to one embodiment of the present invention.

As depicted in FIG. 1 an embodiment of the iontophoretic device of this invention (40) is configured as follows: an anode patch (10), having an anode electrode compartment (11) in ionic communication with a skin contacting compartment (13). The skin contacting compartment (13) and the anode electrode compartment (11) maybe separated by a compartment separation means (membrane) (17). The anode electrode compartment (11) also contains an anode (14) and an electrolyte (anolyte) (15). The skin contacting compartment is attached to the patient's skin (36). A cathode patch (20), having a cathode electrode compartment (21) in ionic communication with a skin contacting compartment (23). The skin contacting compartment (23) and the cathode electrode compartment (21) maybe separated by a compartment separation means (membrane) (27). The cathode electrode compartment (21) also contains an cathode (24) and an electrolyte (catholyte) (25). The skin contacting compartment is attached to the patient's skin (36).

While the present invention has been described in connection with iontophoresis, it should be appreciated that it may be used in connection with other principles of active introduction, i.e., motive forces. Accordingly, the invention is understood to be operative in connection with electrophoresis, which includes the movement of particles in an electric field toward one or the other electric pole (anode or cathode), and electroosmosis, which includes the transport of uncharged compounds due to the bulk migration of water induced by an electric field. Also it should be appreciated that the patient or subject may include humans as well as animals.

The chemical stability of RemiHCl was evaluated in the following manner. RemiHCl was purchased at a pharmacy, marketed under the brand name ULTIVA™ by Glaxo Wellcome, PLC which is a vial of dry powder of 5 milligrams of RemiHCl, glycine and hydrochloric acid buffer. One solution was prepared by diluting a vial with water to provide a RemiHCl concentration of 0.5 milligrams per milliliter ("mg/mL") and another solution was prepared by diluting a vial with a buffer solution to provide a RemiHCl concentration of 0.5 mg/ml. The buffer solution was 0.01 molar HEPES, 0.1 molar sodium chloride, 0.01 percent by weight sodium azide (as a preservative), 0.1 percent by volume of Pluronic P103 surfactant and 2.3 percent by volume polyethylene glycol having a molecular weight of 40 buffered to a pH of 7.4 with sodium hydroxide. The pH of the aqueous dilution was in the range of from 3 to 4. The pH of the buffered solution was 7.4. Samples of the two solutions were maintained at room temperature. After seven days, there was no measurable degradation in the level of RemiHCl in the aqueous solution. However, the RemiHCl in the buffered solution had a half-life of 29.8 as determined by HPLC. Thus, there is an appreciable amount of chemical degradation at a pH which is likely to be encountered in skin.

In addition to the compounds having pH sensitivities which affect their chemical stability, the compounds of formula (I) also contain ester functionality. However, it is known that skin has a number of esterases which cleave ester functional groups. Thus, it would be expected that compounds of formula (I), including RemiHCl, would not pass through the skin intact without first being attacked by one or more esterases in the skin.

Figure 2:
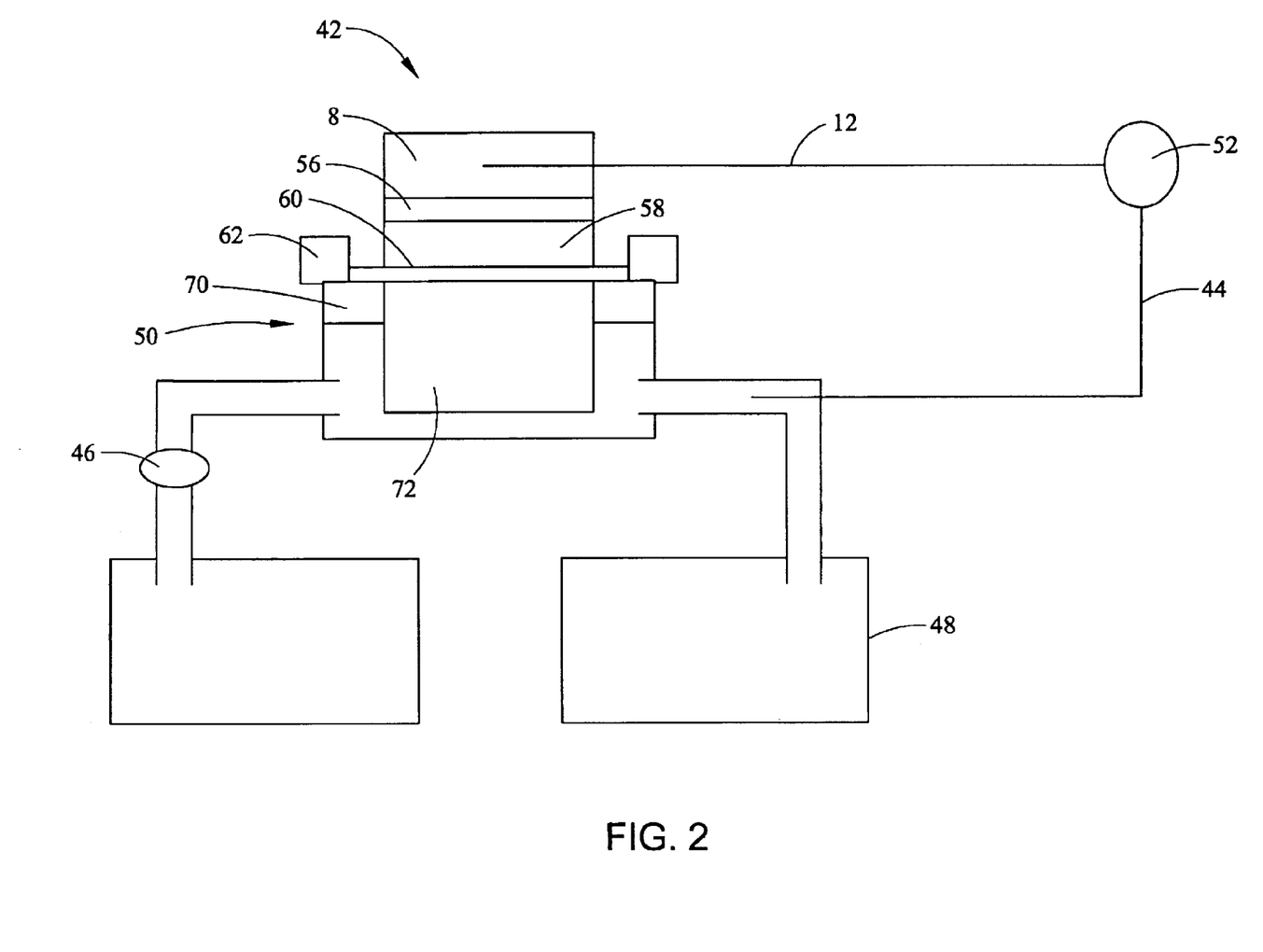
FIG. 2 depicts an in vitro apparatus useful for evaluating iontophoretic delivery.

The in vitro iontophoretic delivery of compounds of formula (I) was evaluated as follows:

Donor electrodes (42) were constructed according to FIG. 2, where the upper compartment (8) had 25 percent by weight IRP69 beads in 10 millimolar sodium chloride in a matrix of 2 percent by weight agarose. The drug reservoir (58) was a 2 $cm^2$ hydrophilic Porex membrane of either 1/16" or 1/8" thickness. The drug reservoir (58) was separated from the upper compartment (8) by a 100 molecular weight cut off ultrafiltrate diaflo membrane (56). The electrodes (44,12) used were silver/silver chloride and they were connected to a power supply (52).

A set of six parallel 2-square centimeter FTC 006 flow-through-cells (50) were constructed by placing a porous Porex support (72) in the cell and covering it with a rubber sealing gasket (70). Samples of porcine skin (60) were dermatomed to a nominal thickness of 1 millimeter and kept under refrigeration. All samples of porcine skin (60) were used within three days of receiving them from the supplier. Atop the rubber sealing gasket (70) was placed a layer of excised porcine skin sealed (60) which was clamped in place with a clamp (62) on the top portion of the cell (50).

RemiHCl solutions were prepared at various concentrations by diluting the purchased 5.0 milligram vials of RemiHCl with water or 10 millimolar acetic acid (as indicated below) to obtain drug concentrations of 2.5, 10 or 20 mg/ml RemiHCl (2.0, 0.5, 0.25 ml dilution volumes respectively). An appropriate volume of RemiHCl solutions for achieving the total amount of compound was applied to the drug reservoir (58) immediately prior to placing the donor electrode (42) on the skin (60). The donor electrode (42) described above was seated on top of the skin (60) and clamped in place to maintain good patch-to-skin contact. A cathode (44) was housed upstream between the cell (50) and a buffer reservoir (48) to avoid contact with the drug. A buffer solution, as prepared above for the stability experiment, was pumped at a flow rate of 0.1 milliliters per minute beneath the Porex support (72) at the bottom of the cell. The flow rate of the buffer solution was controlled by a peristaltic pump (46). The total volume of buffer solution was collected over 1 hour intervals by a fraction collector. Fraction tubes were spiked with 100 microliters of 50 percent acetic acid prior to collection of buffer solution. Cells were run passively for 1 hour with no current, followed by a 24 h current application. Current and voltage profiles were recorded every 5 minutes by a Fluka Hydra Databucket.

The data in Tables I, II and III show the mean flux, in units of micrograms per minute per square centimeter, "$\mu g/min/cm^2$," of RemiHCl detected as determined by analyzing the amount of RemiHCl in the buffer solution. The data reported are the average of three cells run during each experiment. The drug reservoir was loaded with an aqueous RemiHCl solution at the concentration, in milligrams per milliliter, "mg/ml" indicated in the Tables I and II below. The drug reservoir was loaded with RemiHCl, from which the glycine had been previously extracted, dissolved in 10 millimolar acetic acid at the concentration, in milligrams per milliliter, "mg/ml" indicated in the Table III below. The applied current, in microamperes, "$\mu A$," and the total amount of RemiHCl loaded into each drug reservoir in milligrams, "mg" is indicated in the tables below. In experiments 15 and 16, a polyvinylalcohol gel was used instead of a porex pad.

TABLE I

| | | Experiment #1 10 500 1 | | Experiment #2 20 500 2 | | Experiment #3 10 500 3 | | Experiment #4 2.5 500 0.75 | | Experiment #5 2.5 500 0.75 | | Experiment #6 10 500 3 | |
|---|---|---|---|---|---|---|---|---|---|---|---|---|---|
| Time (hrs) | Flux | $\mu g/min/cm^2$ | std. dev. | $\mu g/min/cm^2$ | std. dev. | $\mu g/min/cm^2$ | std. dev. | $\mu g/min/cm^2$ | std. dev. | $\mu g/min/cm^2$ | std. dev. | $\mu g/min/cm^2$ | std. dev. |
| −1.00 | | 0.00 | 0.00 | 0.00 | 0.00 | 0.00 | 0.00 | 0.00 | 0.00 | 0.00 | 0.00 | 0.00 | 0.00 |
| 0.00 | | 0.00 | 0.00 | 0.00 | 0.00 | 0.00 | 0.00 | 0.00 | 0.00 | 0.00 | 0.00 | 0.00 | 0.00 |
| 1.00 | | 0.00 | 0.00 | 0.00 | 0.00 | 0.00 | 0.00 | 0.00 | 0.00 | 0.00 | 0.00 | 0.00 | 0.00 |
| 2.00 | | 0.00 | 0.00 | 0.02 | 0.01 | 0.01 | 0.01 | 0.00 | 0.00 | 0.01 | 0.01 | 0.04 | 0.03 |
| 3.00 | | 0.02 | 0.01 | 0.03 | 0.01 | 0.03 | 0.01 | 0.01 | 0.01 | 0.02 | 0.01 | 0.04 | 0.03 |
| 4.00 | | 0.03 | 0.01 | 0.05 | 0.02 | 0.04 | 0.02 | 0.03 | 0.02 | 0.04 | 0.03 | 0.04 | 0.04 |
| 5.00 | | 0.05 | 0.02 | 0.05 | 0.02 | 0.04 | 0.02 | 0.05 | 0.03 | 0.07 | 0.03 | 0.05 | 0.05 |
| 6.00 | | 0.07 | 0.02 | 0.06 | 0.02 | 0.04 | 0.01 | 0.09 | 0.04 | 0.11 | 0.05 | 0.05 | 0.05 |
| 7.00 | | 0.09 | 0.02 | 0.06 | 0.02 | 0.04 | 0.01 | 0.11 | 0.05 | 0.14 | 0.05 | 0.05 | 0.05 |
| 8.00 | | 0.11 | 0.01 | 0.06 | 0.02 | 0.03 | 0.01 | 0.13 | 0.05 | 0.17 | 0.05 | 0.05 | 0.05 |
| 9.00 | | 0.12 | 0.01 | 0.07 | 0.02 | 0.03 | 0.01 | 0.14 | 0.05 | 0.19 | 0.04 | 0.05 | 0.05 |
| 10.00 | | 0.15 | 0.02 | 0.07 | 0.02 | 0.033 | 0.01 | 0.15 | 0.05 | 0.21 | 0.02 | 0.05 | 0.05 |
| 11.00 | | 0.16 | 0.00 | 0.08 | 0.02 | 0.035 | 0.012 | 0.155 | 0.042 | 0.22 | 0.01 | 0.06 | 0.05 |
| 12.00 | | 0.18 | 0.01 | 0.09 | 0.01 | 0.037 | 0.01 | 0.16 | 0.04 | 0.23 | 0.01 | 0.06 | 0.05 |
| 13.00 | | 0.20 | 0.02 | 0.10 | 0.01 | 0.039 | 0.014 | 0.167 | 0.034 | 0.23 | 0.01 | 0.06 | 0.04 |
| 14.00 | | 0.22 | 0.04 | 0.11 | 0.01 | 0.04 | 0.01 | 0.17 | 0.03 | 0.23 | 0.02 | 0.07 | 0.04 |
| 15.00 | | 0.23 | 0.04 | 0.12 | 0.01 | 0.047 | 0.014 | 0.174 | 0.026 | 0.23 | 0.02 | 0.08 | 0.04 |
| 16.00 | | 0.24 | 0.04 | 0.14 | 0.01 | 0.05 | 0.01 | 0.17 | 0.02 | 0.23 | 0.02 | 0.08 | 0.05 |
| 17.00 | | 0.25 | 0.05 | 0.15 | 0.01 | 0.058 | 0.013 | 0.178 | 0.016 | 0.22 | 0.02 | 0.08 | 0.05 |
| 18.00 | | 0.26 | 0.06 | 0.17 | 0.01 | 0.06 | 0.01 | 0.18 | 0.01 | 0.22 | 0.02 | 0.09 | 0.05 |
| 19.00 | | 0.26 | 0.06 | 0.19 | 0.01 | 0.072 | 0.012 | 0.178 | 0.006 | 0.22 | 0.02 | 0.10 | 0.05 |
| 20.00 | | 0.26 | 0.05 | 0.21 | 0.02 | 0.08 | 0.01 | 0.18 | 0.00 | 0.21 | 0.02 | 0.11 | 0.05 |
| 21.00 | | 0.24 | 0.04 | 0.23 | 0.03 | 0.098 | 0.024 | 0.173 | 0.002 | 0.20 | 0.02 | 0.12 | 0.04 |
| 22.00 | | 0.23 | 0.03 | 0.26 | 0.04 | 0.12 | 0.04 | 0.17 | 0.00 | 0.20 | 0.03 | 0.13 | 0.04 |
| 23.00 | | 0.22 | 0.04 | 0.27 | 0.04 | 0.124 | 0.034 | 0.167 | 0.008 | 0.19 | 0.02 | 0.16 | 0.03 |
| 24.00 | | 0.20 | 0.03 | 0.29 | 0.04 | 0.13 | 0.03 | 0.16 | 0.01 | 0.18 | 0.03 | 0.16 | 0.04 |

TABLE II

| | | Experiment #7 10 500 1 | | Experiment #8 10 0 1 | | Experiment #9 10 1000 1 | | Experiment #10 10 100 1 | |
|---|---|---|---|---|---|---|---|---|---|
| Time (hrs) | Flux | $\mu g/min/cm^2$ | std. dev. | $\mu g/min/cm^2$ | std. dev. | $\mu g/min/cm^2$ | std. dev. | $\mu g/min/cm^2$ | std. dev. |
| −1.00 | | 0.00 | 0.00 | 0.00 | 0.00 | 0.00 | 0.00 | 0.00 | 0.00 |
| 0.00 | | 0.00 | 0.00 | 0.00 | 0.00 | 0.00 | 0.00 | 0.00 | 0.00 |
| 1.00 | | 0.00 | 0.00 | 0.00 | 0.00 | 0.01 | 0.00 | 0.00 | 0.00 |
| 2.00 | | 0.02 | 0.01 | 0.00 | 0.00 | 0.04 | 0.01 | 0.01 | 0.01 |
| 3.00 | | 0.05 | 0.01 | 0.01 | 0.00 | 0.06 | 0.01 | 0.03 | 0.03 |
| 4.00 | | 0.07 | 0.02 | 0.01 | 0.00 | 0.07 | 0.01 | 0.03 | 0.02 |
| 5.00 | | 0.08 | 0.02 | 0.01 | 0.00 | 0.08 | 0.01 | 0.02 | 0.00 |
| 6.00 | | 0.09 | 0.02 | 0.01 | 0.00 | 0.09 | 0.02 | 0.02 | 0.00 |
| 7.00 | | 0.11 | 0.03 | 0.01 | 0.00 | 0.11 | 0.02 | 0.03 | 0.00 |
| 8.00 | | 0.14 | 0.04 | 0.01 | 0.00 | 0.13 | 0.02 | 0.03 | 0.01 |
| 9.00 | | 0.18 | 0.04 | 0.01 | 0.00 | 0.14 | 0.03 | 0.03 | 0.01 |
| 10.00 | | 0.22 | 0.03 | 0.01 | 0.00 | 0.16 | 0.03 | 0.02 | 0.01 |
| 11.00 | | 0.27 | 0.04 | 0.00 | 0.00 | 0.19 | 0.04 | 0.03 | 0.01 |
| 12.00 | | 0.31 | 0.03 | 0.00 | 0.00 | 0.22 | 0.05 | 0.03 | 0.01 |
| 13.00 | | 0.33 | 0.04 | 0.00 | 0.00 | 0.24 | 0.07 | 0.03 | 0.01 |
| 14.00 | | 0.36 | 0.04 | 0.00 | 0.00 | 0.26 | 0.06 | 0.03 | 0.01 |
| 15.00 | | 0.36 | 0.04 | 0.00 | 0.00 | 0.28 | 0.07 | 0.03 | 0.01 |
| 16.00 | | 0.35 | 0.04 | 0.00 | 0.00 | 0.30 | 0.07 | 0.03 | 0.01 |
| 17.00 | | 0.34 | 0.04 | 0.00 | 0.00 | 0.33 | 0.07 | 0.03 | 0.01 |
| 18.00 | | 0.31 | 0.05 | 0.00 | 0.00 | 0.35 | 0.07 | 0.03 | 0.01 |
| 19.00 | | 0.31 | 0.06 | 0.00 | 0.00 | 0.38 | 0.08 | 0.03 | 0.01 |
| 20.00 | | 0.29 | 0.06 | 0.00 | 0.00 | 0.41 | 0.06 | 0.03 | 0.01 |
| 21.00 | | 0.26 | 0.05 | 0.00 | 0.00 | 0.44 | 0.06 | 0.03 | 0.01 |
| 22.00 | | 0.23 | 0.05 | 0.00 | 0.00 | 0.46 | 0.05 | 0.03 | 0.01 |
| 23.00 | | 0.20 | 0.05 | 0.00 | 0.00 | 0.48 | 0.04 | 0.03 | 0.01 |
| 24.00 | | | | | | 0.50 | 0.04 | 0.03 | 0.02 |

TABLE III

| | | Experiment #11 | | Experiment #12 | | Experiment #13 | | Experiment #14 | | Experiment #15 | | Experiment #16 | |
|---|---|---|---|---|---|---|---|---|---|---|---|---|---|
| | mg/ml | 10 | | 10 | | 2.5 | | 20 | | 2.5 | | 10 | |
| | uA | 500 | | 500 | | 500 | | 500 | | 500 | | 500 | |
| | mg | 1 | | 3 | | 0.75 | | 2 | | 0.375 | | 1.5 | |
| Time (hrs) | Flux | $\mu g/min/cm^2$ | std. dev. | $\mu g/min/cm^2$ | std. dev. | $\mu g/min/cm^2$ | std. dev. | $\mu g/min/cm^2$ | std. dev. | $\mu g/min/cm^2$ | std. dev. | $\mu g/min/cm^2$ | std. dev. |
| −1.00 | | 0.00 | 0.00 | 0.00 | 0.00 | 0.00 | 0.00 | 0.00 | 0.00 | 0.00 | 0.00 | 0.00 | 0.00 |
| 0.00 | | 0.00 | 0.00 | 0.00 | 0.00 | 0.00 | 0.00 | 0.00 | 0.00 | 0.00 | 0.00 | 0.00 | 0.00 |
| 1.00 | | 0.00 | 0.00 | 0.00 | 0.00 | 0.00 | 0.00 | 0.00 | 0.00 | 0.00 | 0.00 | 0.00 | 0.00 |
| 2.00 | | 0.00 | 0.00 | 0.00 | 0.00 | 0.00 | 0.00 | 0.00 | 0.00 | 0.00 | 0.00 | 0.00 | 0.00 |
| 3.00 | | 0.00 | 0.00 | 0.01 | 0.02 | 0.00 | 0.00 | 0.00 | 0.00 | 0.01 | 0.00 | 0.01 | 0.01 |
| 4.00 | | 0.00 | 0.00 | 0.01 | 0.01 | 0.01 | 0.01 | 0.01 | 0.01 | 0.02 | 0.00 | 0.02 | 0.01 |
| 5.00 | | 0.01 | 0.00 | 0.02 | 0.03 | 0.01 | 0.01 | 0.02 | 0.01 | 0.03 | 0.01 | 0.03 | 0.01 |
| 6.00 | | 0.01 | 0.00 | 0.02 | 0.03 | 0.01 | 0.01 | 0.02 | 0.01 | 0.04 | 0.01 | 0.03 | 0.02 |
| 7.00 | | 0.01 | 0.00 | 0.02 | 0.03 | 0.01 | 0.00 | 0.03 | 0.01 | 0.05 | 0.01 | 0.04 | 0.02 |
| 8.00 | | 0.02 | 0.01 | 0.02 | 0.03 | 0.02 | 0.01 | 0.03 | 0.01 | 0.06 | 0.01 | 0.04 | 0.02 |
| 9.00 | | 0.03 | 0.01 | 0.02 | 0.02 | 0.03 | 0.01 | 0.02 | 0.00 | 0.07 | 0.01 | 0.04 | 0.02 |
| 10.00 | | 0.06 | 0.02 | 0.01 | 0.02 | 0.04 | 0.01 | 0.02 | 0.01 | 0.07 | 0.01 | 0.05 | 0.01 |
| 11.00 | | 0.06 | 0.02 | 0.01 | 0.02 | 0.05 | 0.02 | 0.02 | 0.00 | 0.09 | 0.01 | 0.06 | 0.01 |
| 12.00 | | 0.08 | 0.02 | 0.01 | 0.02 | 0.06 | 0.02 | 0.02 | 0.01 | 0.10 | 0.01 | 0.06 | 0.00 |
| 13.00 | | 0.09 | 0.02 | 0.01 | 0.01 | 0.07 | 0.02 | 0.03 | 0.01 | 0.11 | 0.01 | 0.08 | 0.02 |
| 14.00 | | 0.11 | 0.03 | 0.01 | 0.01 | 0.08 | 0.03 | 0.03 | 0.01 | 0.10 | 0.03 | 0.08 | 0.02 |
| 15.00 | | 0.12 | 0.02 | 0.02 | 0.02 | 0.09 | 0.04 | 0.03 | 0.02 | 0.10 | 0.03 | 0.08 | 0.01 |
| 16.00 | | 0.12 | 0.02 | 0.02 | 0.02 | 0.10 | 0.04 | 0.04 | 0.02 | 0.10 | 0.03 | 0.10 | 0.02 |
| 17.00 | | 0.13 | 0.02 | 0.03 | 0.02 | 0.10 | 0.04 | 0.05 | 0.02 | 0.09 | 0.02 | 0.10 | 0.02 |
| 18.00 | | 0.15 | 0.03 | 0.03 | 0.02 | 0.11 | 0.05 | 0.05 | 0.03 | 0.08 | 0.02 | 0.11 | 0.02 |
| 19.00 | | 0.15 | 0.03 | 0.04 | 0.02 | 0.11 | 0.04 | 0.06 | 0.03 | 0.07 | 0.02 | 0.11 | 0.02 |
| 20.00 | | 0.17 | 0.03 | 0.04 | 0.02 | 0.12 | 0.04 | 0.07 | 0.03 | 0.07 | 0.00 | 0.12 | 0.02 |
| 21.00 | | 0.16 | 0.03 | 0.05 | 0.02 | 0.12 | 0.04 | 0.07 | 0.04 | 0.07 | 0.02 | 0.11 | 0.02 |
| 22.00 | | 0.18 | 0.03 | 0.06 | 0.02 | 0.11 | 0.03 | 0.08 | 0.04 | 0.06 | 0.03 | 0.12 | 0.02 |
| 23.00 | | 0.19 | 0.03 | 0.07 | 0.02 | 0.12 | 0.03 | 0.09 | 0.04 | 0.06 | 0.03 | 0.12 | 0.02 |
| 24.00 | | 0.20 | 0.02 | 0.08 | 0.03 | 0.11 | 0.03 | 0.10 | 0.05 | 0.06 | 0.03 | 0.12 | 0.02 |

The in vivo iontophoretic delivery of compounds of formula I was evaluated as follows.

ULTIVA® brand remifentanil was diluted with water to a concentration of 5 mg/ml. 200 ul of this solution was added to a 2 cm² monolithic polyvinylpyrrolidone gel anode without added salt. The gel containing the RemiHCl was allowed to equilibrate for 2–6 hours, to allow complete absorption of the solution and equilibration of the RemiHCl in the gel. An indifferent electrode was attached to a polyvinylpyrrolidone gel. Anodic and cathodic patches were applied dorsally along either side of the spine of 5 guinea pigs, chemically depilated the previous day, and held tightly in place with VetWrap bandages. Baseline responses for each animal were scored before patch application at t=−10 min, and immediately after patch application and wrapping, but before application of current at t=0. A 500 uA (250 uA/cm²) curruit was applied and maintained for 60 min. Supraspinal and motor response were evaluated at ten minute time intervals during the 1 hour current application, and for 20 minutes thereafter.

In baseline evaluations, all animals showed brisk responses to stimuli both before patch application, and with the patches in place. This confirms that the passive patch and overwrap were not interfering with the normal movements and behaviors of the animals. After current application animals showed visibly decreased activity almost immediately. The responses evaluated were pinna reflex (ear twitch), corneal reflex, hind limb flexor response, and spontaneous and evoked movement (startle reflex). Responses were well abrogated in all animals within 10 minutes. Effects continued to increase until an apparent plateau was reached around 25 miutes. This reduced level of response was maintained throughout the duration of current. The most reproducibly affected responses were pinna and corneal reflex which was scored as totally absent in all animals during the course of testing. Spontaneous movement was also dramatically affected in some animals which remained nearly motionless during testing. Others still showed a propensity to move although at a slowed pace with awkward motions. Startle reflex appeared the least affected during testing. Motor reflexes were only partially impaired. All effects were rapidly abrogated after current was stopped. Within ten minutes almost all animals had returned to a normal level of activity and response to external stimuli.

We claim:

1. An iontophoretic device comprising:
   (a) a donor reservoir comprising a matrix material and, distributed in said matrix material, a pharmaceutically acceptable amount of at least one compound selected from compounds of the formula (I)

wherein:
   X is a member selected from the group consisting of: alkoxy-carbonyl-lower alkyl, lower alkyl-carbonyloxy-lower alkyl, alkenyloxy-carbonyl-lower alkyl, and $(C_{1-2})$alkoxy-$(C_{1-2})$alkoxy-carbonyl-lower alkyl;
   Ar is a member selected from the group consisting of phenyl, and mono-, di- and tri-substituted phenyl, wherein each substituent is independently selected from the group consisting of halo, lower alkyl, lower alkoxy and trifluoromethyl;

R is a member selected from the group consisting of lower alkyl, $OCH_3$ and lower alkoxy-lower alkyl;

$R^1$ is a member selected from the group consisting of hydrogen, and lower alkoxy-carbonyl; and $R^2$ is a member selected from the group consisting of hydrogen and methyl, and the optically active and cis-trans isomers thereof, and the acid addition salts of said compounds and isomers;

(b) a current distributing member in electrical communication with the donor reservoir;

(c) an indifferent electrode; and (d) an electrical power source in electrical connection with the current distributing member and the indifferent electrode.

2. The iontophoretic device of claim 1 wherein X is alkoxy-carbonyl-lower alkyl.

3. The iontophoretic device of claim 1 wherein the at least one compound is the hydrochloride salt of the compound of formula (I) wherein X is $CH_2CH_2COOCH_3$, R is $OCH_3$, $R^1$ and $R^2$ are both hydrogen, and Ar is phenyl.

4. The iontophoretic device of claim 1 wherein the matrix material is a polymer gel.

5. The iontophoretic device of claim 1 wherein the matrix material is crosslinked polyvinylpyrrolidone.

6. A method for preparing an iontophoretic reservoir comprising:

distributing in a matrix material an effective amount of at least one compound of the formula (I)

wherein:

X is a member selected from the group consisting of: alkoxy-carbonyl-lower alkyl, lower alkyl-carbonyloxy-lower alkyl, alkenyloxy-carbonyl-lower alkyl, and $(C_{1-2})$alkoxy-$(C_{1-2})$alkoxy-carbonyl-lower alkyl;

Ar is a member selected from the group consisting of phenyl, and mono-, di- and tri-substituted phenyl, wherein each substituent is independently selected from the group consisting of halo, lower alkyl, lower alkoxy and trifluoromethyl;

R is a member selected from the group consisting of lower alkyl, $OCH_3$ and lower alkoxy-lower alkyl;

$R^1$ is a member selected from the group consisting of hydrogen, and lower alkoxy-carbonyl; and $R^2$ is a member selected from the group consisting of hydrogen and methyl, and the optically active and cis-trans isomers thereof, and the acid addition salts of said compounds and isomers.

7. The method of claim 6 wherein X is alkoxy-carbonyl-lower alkyl.

8. The method of claim 6 wherein the at least one compound is the hydrochloride salt of the compound of formula (I) wherein X is $CH_2CH_2COOCH_3$, R is $OCH_3$, $R^1$ and $R^2$ are both hydrogen, and Ar is phenyl.

9. The method of claim 6 wherein the matrix material is a polymer gel.

10. The method of claim 6 wherein the matrix material is crosslinked polyvinylpyrrolidone.

11. The method of claim 6, wherein the at least one compound is distributed in the matrix in an amount of from 0.01 milligrams to 1000 milligrams.

* * * * *

UNITED STATES PATENT AND TRADEMARK OFFICE
CERTIFICATE OF CORRECTION

| | | |
|---|---|---|
| PATENT NO. | : 6,858,018 B1 | Page 1 of 2 |
| APPLICATION NO. | : 09/162301 | |
| DATED | : February 22, 2005 | |
| INVENTOR(S) | : Green et al. | |

It is certified that error appears in the above-identified patent and that said Letters Patent is hereby corrected as shown below:

On the Title Page, Item -56- Pg. 2

<u>OTHER PUBLICATIONS</u>:

Line 6, delete "fentanlyl" and insert --fentanyl-- therefor.

Line 21, delete "Absoption" and insert --Absorption-- therefor.

Col. 5, line 23, delete "8:422446" and insert --8:422-446-- therefor.

Col. 6, line 16, delete "amount of from" and insert --amount from-- therefor.

Col. 6, line 46, delete "use" and insert --used-- therefor.

Col. 6, line 57, delete "amount of from" and insert --amount from-- therefor.

Col. 6, line 58, delete "amount of from" and insert --amount from-- therefor.

Col. 9, line 29, delete "to" therefor.

Col. 11, line 3, delete "an" and insert --a-- therefor.

Col. 17, line 2, claim 1, delete "–$OCH_3$ and–" and insert --$OCH_3$ and-- therefor.

Col. 18, line 37, claim 11, delete "claim 6," and insert --claim 6-- therefor.

UNITED STATES PATENT AND TRADEMARK OFFICE
CERTIFICATE OF CORRECTION

PATENT NO. : 6,858,018 B1
APPLICATION NO. : 09/162301
DATED : February 22, 2005
INVENTOR(S) : Green et al.

It is certified that error appears in the above-identified patent and that said Letters Patent is hereby corrected as shown below:

Col. 18, line 38, claim 11, delete "amount of from" and insert --amount from-- therefor.

Signed and Sealed this

Fifteenth Day of April, 2008

JON W. DUDAS
*Director of the United States Patent and Trademark Office*